United States Patent [19]

Lee

[11] Patent Number: 5,308,612
[45] Date of Patent: May 3, 1994

[54] USES OF POLYSTYRENESULFONATE AND RELATED COMPOUNDS AS INHIBITORS OF TRANSACTIVATING TRANSCRIPTION FACTOR (TAT) AND AS THERAPEUTICS FOR HIV INFECTION AND AIDS

[75] Inventor: Jung J. Lee, Albany, N.Y.

[73] Assignee: Blue Marble Research, Inc., Albany, N.Y.

[21] Appl. No.: 925,452

[22] Filed: Aug. 12, 1992

[51] Int. Cl.$^5$ ............... A01N 25/02; A61K 31/74
[52] U.S. Cl. ................... 424/78.35; 424/78.1; 514/885
[58] Field of Search ............ 424/78.01, 7.1, 9; 526/287; 514/885; 422/44

[56] References Cited

U.S. PATENT DOCUMENTS

| | | | |
|---|---|---|---|
| 4,530,964 | 7/1985 | Machovich et al. | 526/287 |
| 4,762,715 | 8/1988 | Lukas et al. | 424/145 |
| 4,783,964 | 7/1985 | Neushul | 514/885 |
| 5,149,523 | 9/1992 | Lundberg | 424/78.1 |
| 5,223,258 | 6/1993 | Machida et al. | 514/835 |

OTHER PUBLICATIONS

Hallinan et al, 1981, vol. 5, pp. 97–101 Cancer Biochem. Biophys.

Primary Examiner—Thurman K. Page
Assistant Examiner—Peter F. Kulkosky
Attorney, Agent, or Firm—James Creighton Wray

[57] ABSTRACT

The uses of polystyrenesulfonate and related compounds to inhibit HIV Tat function/replication and for therapy of HIV/AIDS.

11 Claims, No Drawings

USES OF POLYSTYRENESULFONATE AND RELATED COMPOUNDS AS INHIBITORS OF TRANSACTIVATING TRANSCRIPTION FACTOR (TAT) AND AS THERAPEUTICS FOR HIV INFECTION AND AIDS

BACKGROUND OF THE INVENTION

Acquired Immune Deficiency Syndrome(AIDS) is believed to be caused by the HIV family of retroviruses as well as other still un-identified factors. The virion or its envelop protein, gp120, binds to the CD4 molecule on the surface of CD4+ immune cells to gain entry. Its gene, an RNA, is transcribed to DNA by its Reverse Transcriptase(RT), and it is integrated into the host cell genome, becoming a part of the host cell.

When the infected cell is activated, the guest genome is also replicated. The HIV protein, Tat, is required for the HIV transcription. Blockage of Tat inhibits HIV replication in acute and chronic infection.

During the latency period of eight years on the average, the helper T4 lymphocytes, whose function is to mount a cellular immune defense against foreign invaders, die off slowly, exposing the host to various bacterial infections, and eventually, through a not-yet-well-known mechanism, causing damage to the brain and the central nervous system. Infected lymphocytes secrete Tat and an oncoprotein, which drive tumorigenesis/angiogenesis in AIDS-associated Kaposi's sarcoma(KS).

The only drug which has been found to be useful clinically is AZT, a nucleoside, which is a chain terminator in the transcription. Its clinical benefit is still not definitively established: it develops drug resistance by mutating the RT and also its toxicity to the host is severe. Combination therapy using mixed nucleosides at lower doses is the current practice, without proven efficacy.

This has occasioned an intense search for non-nucleoside and non-protein/peptide drugs. Recently, diazepines have been found to be active against RT and Tat. Inhibitors of the HIV protease have also been developed. But, none have reached the market. Some diazepine analogues, however, are well-known psychotrophic and neurotrophic compounds. One of the side effects has been immunodeficiency, which caused multiple deaths before it was recognized.

DESCRIPTION OF THE INVENTION

A synthetic polyanion, polystyrenesulfonate (PSS), sequesters Tat (HIV) and also blocks viral entry, and thus protects CD4+ T lymphocytes from destruction by HIV. PSS and related compounds are used for inhibition of Tat and HIV replication, and HIV adhesion and entry into the immune cells, for the therapy of HIV infection and AIDS, for the therapy of AIDS-Kaposi's sarcoma and for inhibition of tumorigenesis, angiogenesis and metastasis, and for anti-adhesion and thrombolytic actions. The use of labelled PSS for diagnostic and research purposes are also described and claimed.

This invention concerns the uses and applications of polystyrenesulfonate (PSS) and related compounds for the purpose of antogonizing the transactivating transcription factor (Tat) of Human Immunodeficiency Virus (HIV) to block its replication and to block viral adhesion and infection. The processes of synthesizing PSS and the related compounds specified below are known arts. However, the therapeutic uses are not known, and thus comprise the novelty of this invention.

PSS is a common compound. However, its activity against viral replication/cell death is entirely novel. It consists of neutral salt of a strong organic acid, sulfonate, pendant from the strongly hydrophobic polystyrene backbone.

The chemistry and processes to manufacture this compound are known in textbooks such that its molecular weights can be controlled within better than five percent deviation and all chemical groups can be manipulated regarding their chemical and physical, including chiral, properties.

Tat is a strongly basic protein of 10.8 kiloDalton(kD), containing several hydrophobic amino acid residues and thiol groups. One of the basic groups, an arginine, has been shown to bind to the RNA(TAR) of HIV causing a large conformational change, which culminates in transcription activation. The sulfonate anion and the arginine cation bind with a very high affinity, enhanced by hydrophobic environment contributed by both the protein and PSS.

Secreted Tat will be instantly sequestered by PSS. Thus, blockage of HIV transcription/replication by PSS will protect the immune cells from destruction by the virus and inhibit development of AIDS.

Since PSS sequesters Tat, it can inhibit tumorigenesis and angiogenesis in AIDS-associated KS.

The facts that a sulfated polysaccharide, dextransulfate, of 8 kiloDalton(kD), blocked HIV binding to the cell, that a sulfated polysaccharide-peptido glycan of 30 kD has been shown to inhibit angiogenesis by AIDS-KS, that one of the major components of the extracellular matrix is heparan sulfate and that heparin sulfate has thrombolytic activity, suggest that the mechanism of PSS action may involve its anti-adhesion action and thus thrombolytic potential.

Furthermore, these adhesion functions require the calcium channel activation. Calcium and the related ion channel protein polypeptide chains are woven through the surface membrane repeatedly, and the transmembrane segments are stabilized by ion pair formation between the numerous cationic amino acid residues with the anionic residues. Thus, there is a distinct potential PSS will complex these cationic sites and block the channel activity.

EXAMPLE 1

PSS Binds/Sequesters Tat

When approximately 10 $\mu$M solution of Tat is mixed with equimolar concentration of 16 kD PSS in water around pH 7, and the mixture is chromatographed or electrophoresed on a nondenaturing gel, the Tat protein band will disappear and it will be found bound to the PSS band. When Tat protein is trypsinized and chromatographed using, for example, HPLC, several peptide bands are generated. However, if PSS was added before trypsin, there is no peptide band since PSS sequestered Tat. By titration and appropriate plotting, the stoichiometry and binding strength can be determined.

EXAMPLE 2

PSS Protects Immune Cells from Destruction by HIV

When PSS of 16 kD is added in $\mu$M range to cultured CD4+ cell lines(ca $10^6$ cells) such as H9, CEM and U379, and human peripheral blood monocytes before and soon after HIV infection, the viral entry and replication are inhibited as shown by blockage of cell death-(measured by tetrazolium dye exclusion test for cell viability) and absence of the viral gag antigen, p24(measured by antigen-capture ELISA or flow cytometry).

EXAMPLE 3

PSS Inhibits Tumorigenesis/Angiogenesis in AIDS-KS

The in-vitro proliferation of AIDS-KS cells under the influence of activated/infected CD4+ T-cell conditioned media is inhibited by PSS as determined by microscopy and inhibition of total protein synthesis. Angiogenesis induced by AIDS-KS cells on chick chorioallantoic membranes is inhibited by PSS as determined by microscopy.

Polystyrenesulfonate and related compounds are used to inhibit HIV Tat function and replication and for therapy of HIV and AIDS.

Therapeutic uses of PSS and related compounds of different molecular weights, chiralities, counter ions, hydrophobicity, cation contents (zwitterions) and anions for inhibition of Tat, viral replication, HIV adhesion and infection and related causatives, AIDS, and related diseases are included in the invention.

The above compounds plus their labelled counterparts which are labelled atomically with radioactive or heavy atoms or molecularly with fluorescence probes, ELISA, or monoclonal antibodies have research and diagnostic uses.

The compounds have therapeutic uses for AIDS-associated kaposi's sarcoma and lymphomas, and for related tumorigenesis, angiogenesis and metastasis, because the etiology of AIDS-KS is believed to be due to adhesion of HIV proteins, which is inhibited by PSS.

The compounds have therapeutic uses for anti-adhesion, anti-aggregation, and anti-coagulant and blood thinning purposes.

The following references are cited as background material:

U.S. Pat. No. 5,069,899: Whitbourne, :"Anti-Thrombogenic, Anti-Microbial Compositions Containing Heparin", Dec. 3, 1991.

Other References

"Dextran Sulfate Suppression of Viruses in the HIV Family: Inhibition of Virion Binding to CD4 Cells", Mitsuya, H., Looney, D. J., Kuno, S., Ueno, R., Wong-Staal, F., Broder, S., Science 240, 646(1988).

"Inhibition of Development of Kaposi's Sarcoma-Related Lesions by a Bacterial Cell Wall Complex", Nakamura, S., Sakurada, S., Salahuddin, S. Z., Osada, Y., Tanaka, N. G., Sakamoto, N., Sekiguchi, M., Gallo, R. C., Science 255, 1437(1992).

"Conformation of the TAR RNA-Arginine Complex by NMR Spectroscopy", Puglisi, J. D., Tan, R., Calnan, B. J., Frankel, A. D., Wiliamson, J. R., Science 257, 76(1992).

"Inhibition of HIV Replication in Acute and Chronic Infections in Vitro by a Tat Antagonist", Hsu, M.-C., Schutt, A. D., Holly, M., Slice, L. W., Sherman, M. I., Richman, D. D., Potash, M. J., Volsky, D. J., Science 254, 1799(1991).

"Structure and Function of Voltage-Sensitive Ion Channels", Catterall, W. A., Science 242, 50(1988).

I claim:

1. The method of treating HIV retrovirus infected cells, comprising providing polystyrenesulfonate (PSS) to the patient and sequestering transactivating transcription factor (Tat) of human immunodeficiency virus (HIV) with said (PSS) in order to block replication of the HIV, and to block blocking viral adhesion and entry into not-yet-infected immune cells and tissues by said (HIV) virus.

2. The method of claim 1, the sequestering comprising blocking of the Tat via binding arginine in the Tat to sulfonate ions from the PSS, said sequestering also comprising hydrophobic interactions between the polystyrene backbone and hydrophobic amino residues.

3. The method of claim 1, further comprising inhibiting development of acquired immune deficiency syndrome (AIDS) by protecting immune cells from destruction by HIV virus by blocking transcription and replication of the HIV virus by PSS.

4. The method of claim 1, further comprising inhibiting tumorigenesis and angiogenesis in AIDS-associated Kaposi's sarcoma.

5. The method of claim 1, in which anti-adhesion and thrombolytic action is provided.

6. The method of treating HIV retrovirus infected cells, comprising providing PSS to the cells and sequestering transactivating transcription factor (Tat) of human immunodeficiency virus (HIV) for blocking replication of the HIV.

7. The method of claim 6, wherein the sequestering comprises blocking the Tat by binding arginine in the Tat to sulfonate ions, said sequestering also comprising hydrophobic interactions between the PSS backbone and hydrophobic amino residues.

8. The method of claim 6, further comprising inhibiting development of acquired immune deficiency syndrome (AIDS) by protecting immune cells from destruction by HIV virus wherein entry by PSS blocks TAT and viral adhesion, transcription and replication of the HIV virus being inhibited.

9. The method of claim 6, further comprising inhibiting tumorigenesis and angiogenesis in AIDS-associated Kaposi's sarcoma.

10. The method of claim 6, further comprising anti-adhesion and thrombolytic action.

11. The method of claim 7, wherein the treating comprises protecting CD4+ T lymphocytes and other cells which harbor HIV from destruction by HIV, as well as from HIV protein-induced tumorigenesis.

* * * * *

UNITED STATES PATENT AND TRADEMARK OFFICE
CERTIFICATE OF CORRECTION

PATENT NO. : 5,308,612

DATED : May 3, 1994

INVENTOR(S) : Jung J. Lee

It is certified that error appears in the above-identified patent and that said Letters Patent is hereby corrected as shown below:

Column 1, line 64, change "antogonizing" to --antagonizing--.

Signed and Sealed this

Sixth Day of September, 1994

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,308,612
DATED : May 3, 1994
INVENTOR(S) : Jung J. Lee

It is certified that error appears in the above-indentified patent and that said Letters Patent is hereby corrected as shown below:

Column 4:

Claim 1, line 16, delete "to block".

Claim 8, line 48, change "TAT" to --Tat--.

Signed and Sealed this

Twenty-first Day of March, 1995

Attest:

BRUCE LEHMAN

Attesting Officer

Commissioner of Patents and Trademarks